US012564391B2

(12) United States Patent
Xu et al.

(10) Patent No.: US 12,564,391 B2
(45) Date of Patent: Mar. 3, 2026

(54) SURGICAL ROBOT SYSTEM

(71) Applicant: BEIJING SURGERII ROBOTICS COMPANY LIMITED, Beijing (CN)

(72) Inventors: Kai Xu, Beijing (CN); Ke Xiong, Beijing (CN); Wulin Li, Beijing (CN); Shu'an Zhang, Beijing (CN)

(73) Assignee: BEIJING SERGERII ROBOTICS COMPANY LIMITED, Beijing (CN)

( * ) Notice: Subject to any disclaimer, the term of this patent is extended or adjusted under 35 U.S.C. 154(b) by 503 days.

(21) Appl. No.: 18/009,502

(22) PCT Filed: Mar. 24, 2021

(86) PCT No.: PCT/CN2021/082651
§ 371 (c)(1),
(2) Date: Dec. 9, 2022

(87) PCT Pub. No.: WO2022/001224
PCT Pub. Date: Jan. 6, 2022

(65) Prior Publication Data
US 2023/0310102 A1 Oct. 5, 2023

(30) Foreign Application Priority Data

Jun. 30, 2020 (CN) .......................... 202010617376.2
Jul. 23, 2020 (CN) ......................... 202010716439.X
Jul. 23, 2020 (CN) .......................... 202010727664.3

(51) Int. Cl.
*A61B 17/00* (2006.01)
*A61B 34/30* (2016.01)

(52) U.S. Cl.
CPC .... *A61B 17/00* (2013.01); *A61B 2017/00398* (2013.01); *A61B 2034/304* (2016.02); *A61B 2034/305* (2016.02)

(58) Field of Classification Search
CPC .............. A61B 17/00; A61B 2034/304; A61B 2034/305; A61B 2017/00398
(Continued)

(56) References Cited

U.S. PATENT DOCUMENTS

| | | |
|---|---|---|
| 2010/0224022 A1 | 9/2010 | Choi et al. |
| 2019/0290310 A1 | 9/2019 | Klein |
| 2020/0281787 A1* | 9/2020 | Ruiz ...................... A61B 34/37 |

FOREIGN PATENT DOCUMENTS

| | | |
|---|---|---|
| CN | 101862223 A | 10/2010 |
| CN | 102458295 A | 5/2012 |

(Continued)

OTHER PUBLICATIONS

International Search Report and Written Opinion in related PCT Application No. PCT/CN2021/082651 dated Jun. 23, 2021 (11 pages).

(Continued)

*Primary Examiner* — Aaron F Roane
(74) *Attorney, Agent, or Firm* — Bayes PLLC

(57) ABSTRACT

A surgical robot system includes a platform and at least one positioning arm. The at least one positioning arm each includes a first cross arm and a first rotary joint, the first rotary joint is arranged in the first cross arm or the platform, a proximal end of the first cross arm is rotatably connected to the platform via the first rotary joint, and the first cross arm is operable to rotate about a longitudinal axis relative to the platform. By overlapping first cross arms of a pair of positioning arms and coaxially connecting the first cross arms to the platform, the longitudinal space occupation of the positioning arms can be reduced, and the risk of interference and collision between the positioning arms is reduced.

20 Claims, 10 Drawing Sheets

(58) Field of Classification Search
USPC ............................................................. 606/1
See application file for complete search history.

(56) References Cited

FOREIGN PATENT DOCUMENTS

| | | | |
|---|---|---|---|
| CN | 106236276 | A | 12/2016 |
| CN | 206151581 | U | 5/2017 |
| CN | 107639627 | A | 1/2018 |
| CN | 109381263 | A | 2/2019 |
| CN | 109730778 | A | 5/2019 |
| CN | 209916197 | U | 1/2020 |
| CN | 210354771 | U | 4/2020 |
| EP | 2433585 | A1 | 3/2012 |
| JP | 2012527276 | A | 11/2012 |
| KR | 20120068768 | A | 6/2012 |
| KR | 20150023273 | A | 3/2015 |
| WO | 2014028703 | A1 | 2/2014 |
| WO | 2016164824 | A1 | 10/2016 |

OTHER PUBLICATIONS

Extended European Search Report in related European Application No. 21832198.2 dated Jun. 21, 2024 (7 pages).
Search Report in related Chinese Application No. 2021800344093, dated Mar. 24, 2025 (3 pages).
Office Action in related Canadian Application No. 3173577 dated Feb. 27, 2024 (4 pages).
Office Action in related Japanese Application No. 2022-580283 dated Dec. 26, 2023 (6 pages).
Search Report in related Korean Application No. 10-2022-7041009 dated Feb. 25, 2025 (6 pages).

* cited by examiner

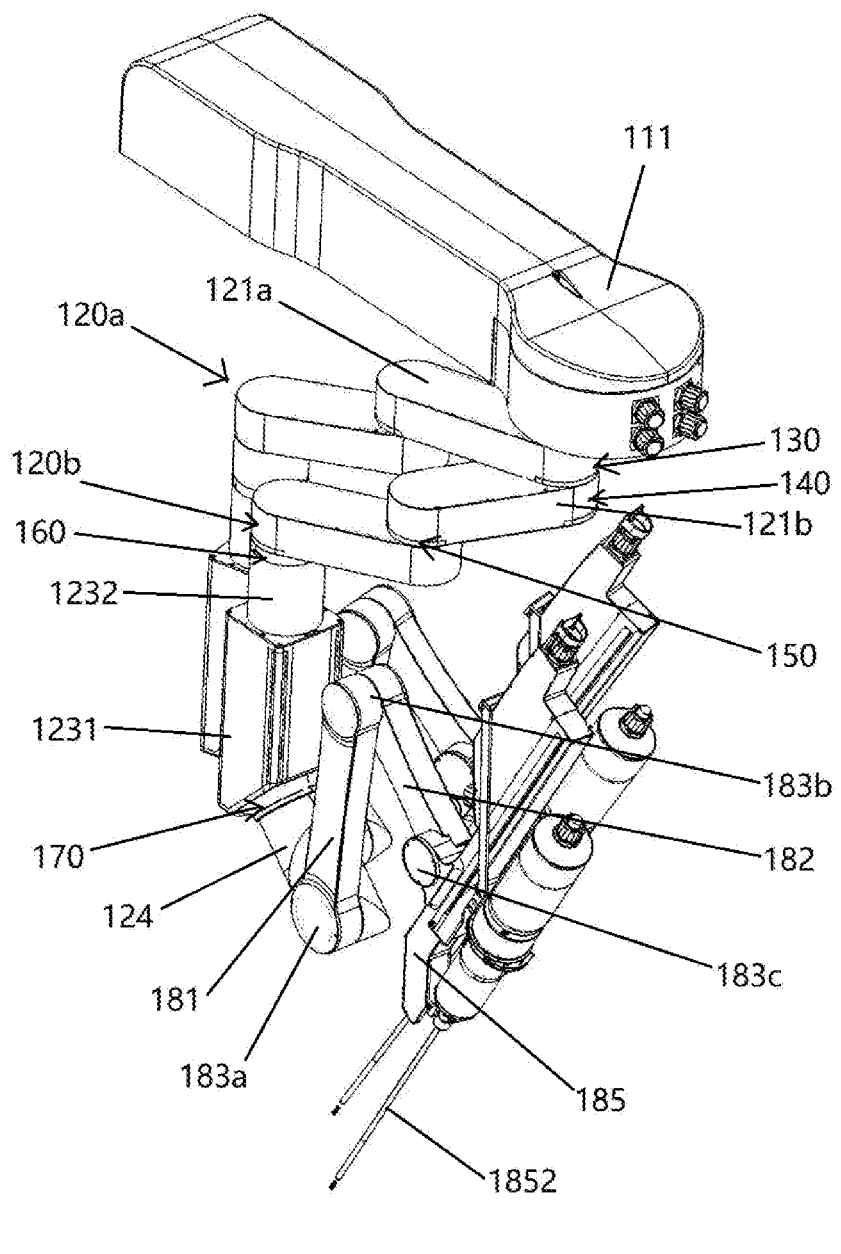
FIG.    2

111
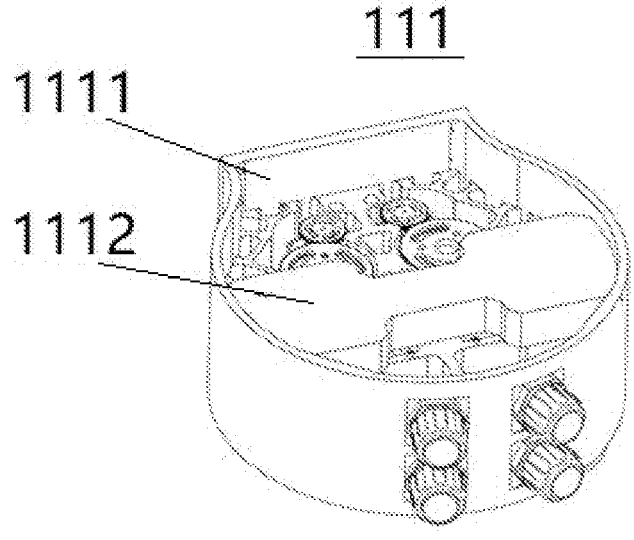
FIG.    3
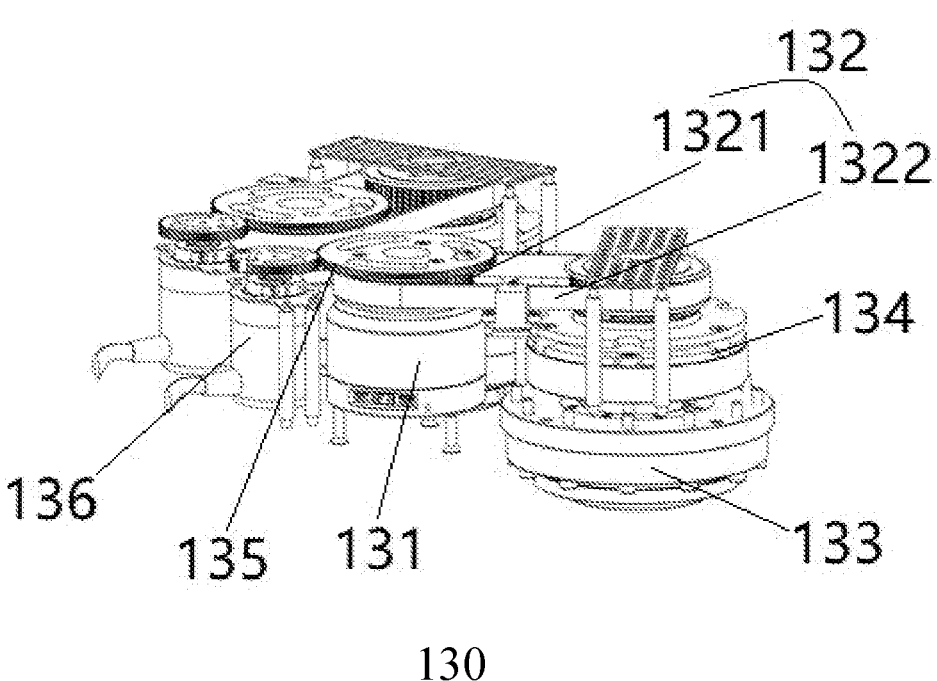
130
FIG.    4

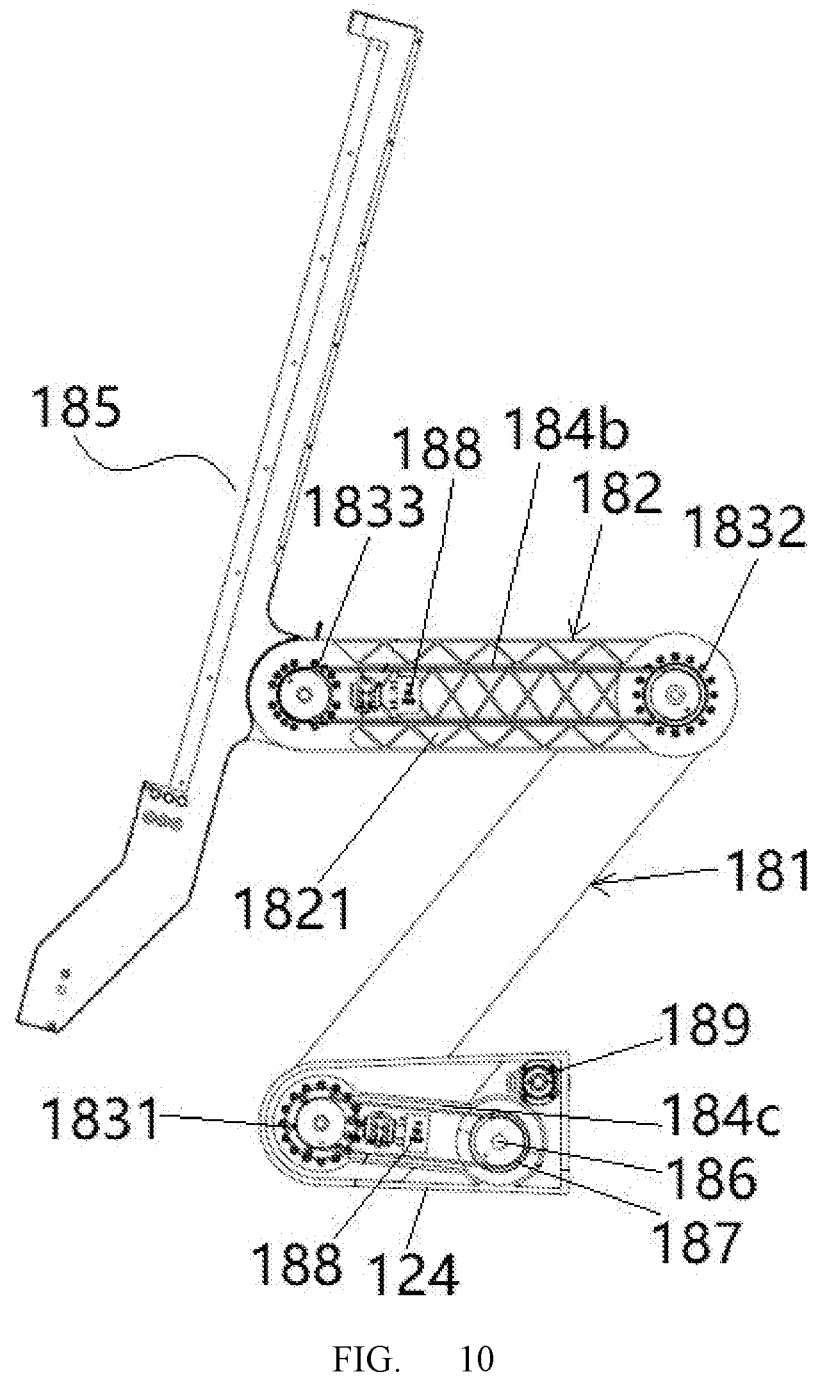
FIG.    10

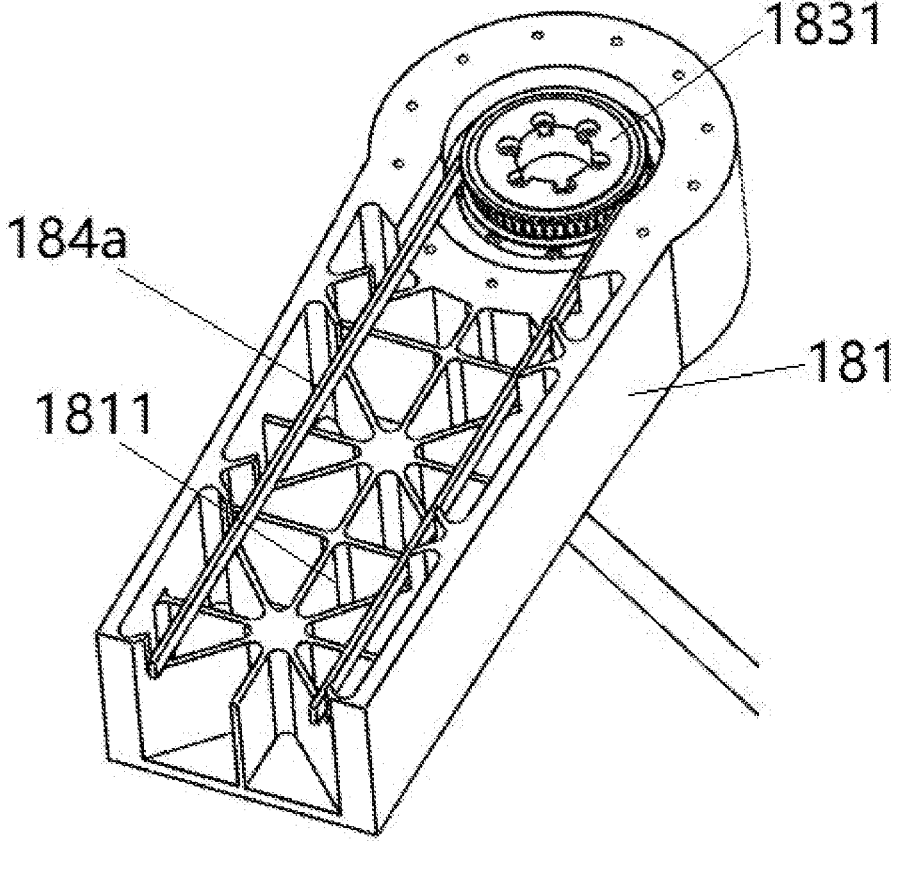
FIG.    11

SURGICAL ROBOT SYSTEM

CROSS-REFERENCE TO RELATED APPLICATIONS

The present application is a national stage of International Application No. PCT/CN2021/082651, filed on Mar. 24, 2021, which claims priority to Chinese Patent Application No. 202010617376.2, filed on Jun. 30, 2020; Chinese Patent Application No. 202010716439.X, filed on Jul. 23, 2020; and Chinese Patent Application No. 202010727664.3, filed on Jul. 23, 2020. The entire contents of each of the above-identified applications are expressly incorporated herein by reference.

TECHNICAL FIELD

The present disclosure relates to the field of medical instruments, and in particular, to a surgical robot system.

BACKGROUND

Compared with conventional surgery, endoscopic minimally invasive surgery has been widely used because of its small surgical trauma and fast postoperative recovery. In an existing endoscopic surgical robot system, a surgical instrument is carried by a positioning arm. According to different patients and surgical procedures, the positioning arm needs to be adjusted and positioned before or during a surgery, so that the surgical instrument is adjusted to a designated position. During the surgery, a chief surgeon uses a teleoperation mode to control a surgical effector at an end of the surgical instrument to implement surgeries in different sites. For the surgical robot system, a positioning ability of the positioning arm in an in-vitro space is directly related to whether a surgical robot can implement various surgical procedures.

SUMMARY

In some embodiments, the present disclosure provides a surgical robot system, comprising: a platform; and at least one positioning arm, comprising a first cross arm and a first rotary joint, wherein the first rotary joint is arranged in the first cross arm or the platform, a proximal end of the first cross arm is rotatably connected to the platform via the first rotary joint, and the first cross arm is operable to rotate about a longitudinal axis relative to the platform.

BRIEF DESCRIPTION OF DRAWINGS

To illustrate technical solutions in embodiments of the present disclosure more clearly, a brief introduction to the accompanying drawings required in the description of the embodiments of the present disclosure will be provided below. The accompanying drawings in the following description show only some embodiments of the present disclosure, and those of ordinary skill in the art may further obtain other embodiments according to the content of the embodiments of the present disclosure and these accompanying drawings without involving any inventive effort.

FIG. 2 shows a schematic structural diagram of a positioning arm according to some embodiments of the present disclosure;

FIG. 3 shows a schematic structural diagram of a platform according to some embodiments of the present disclosure;

FIG. 4 shows a partial schematic diagram of a first rotary joint of a first positioning arm according to some embodiments of the present disclosure;

FIG. 10 shows a rear view of a remote center motion mechanism according to some embodiments of the present disclosure; and FIG. 11 shows a schematic diagram of a partial structure of a movable arm according to some embodiments of the present disclosure.

DETAILED DESCRIPTION

To make the technical problems solved by the present disclosure, and the technical solutions used and achieved technical effects of the present disclosure clearer, the technical solutions of the embodiments of the present disclosure will be further described in detail below with reference to the accompanying drawings. Obviously, the described embodiments are only exemplary embodiments, but not all embodiments, of the present disclosure.

In the description of the present disclosure, it should be understood that the orientations or positional relationships indicated by the terms "center", "upper", "lower", "left", "right", "vertical", "horizontal", "inner", "outer", and the like are based on the orientations or positional relationships shown in the accompanying drawings, and are only for ease of describing the present disclosure and simplifying the description, rather than indicating or implying that the device or element referred to must have a specific orientation or be constructed and operated in a specific orientation, and therefore cannot be construed as limiting the present disclosure. In addition, the terms "first" and "second" are used for descriptive purposes only, and cannot be construed as indicating or implying relative importance. In the description of the present disclosure, it should be noted that, unless otherwise specified and defined, the term "mount", "connected", and "connect", or "couple" should be comprehended in a broad sense. For example, the term may be a fixed connection or a detachable connection; or may be a mechanical connection or an electrical connection; may be a direct connection or an indirect connection via an intermediate medium; or may be internal communication between two elements. For those of ordinary skill in the art, specific meanings of the foregoing terms in the present disclosure may be understood based on specific situations. In the present disclosure, the end close to an operator (e.g., a surgeon) is defined as a proximal end, a proximal portion, a rear end, or a rear portion, and the end close to a surgical patient is defined as a distal end, a distal portion, a front end, or a front portion. It may be understood by those skilled in the art that the embodiments of the present disclosure may be used for a medical instrument or a surgical robot, and may also be used for another non-medical device.

Figure 1:
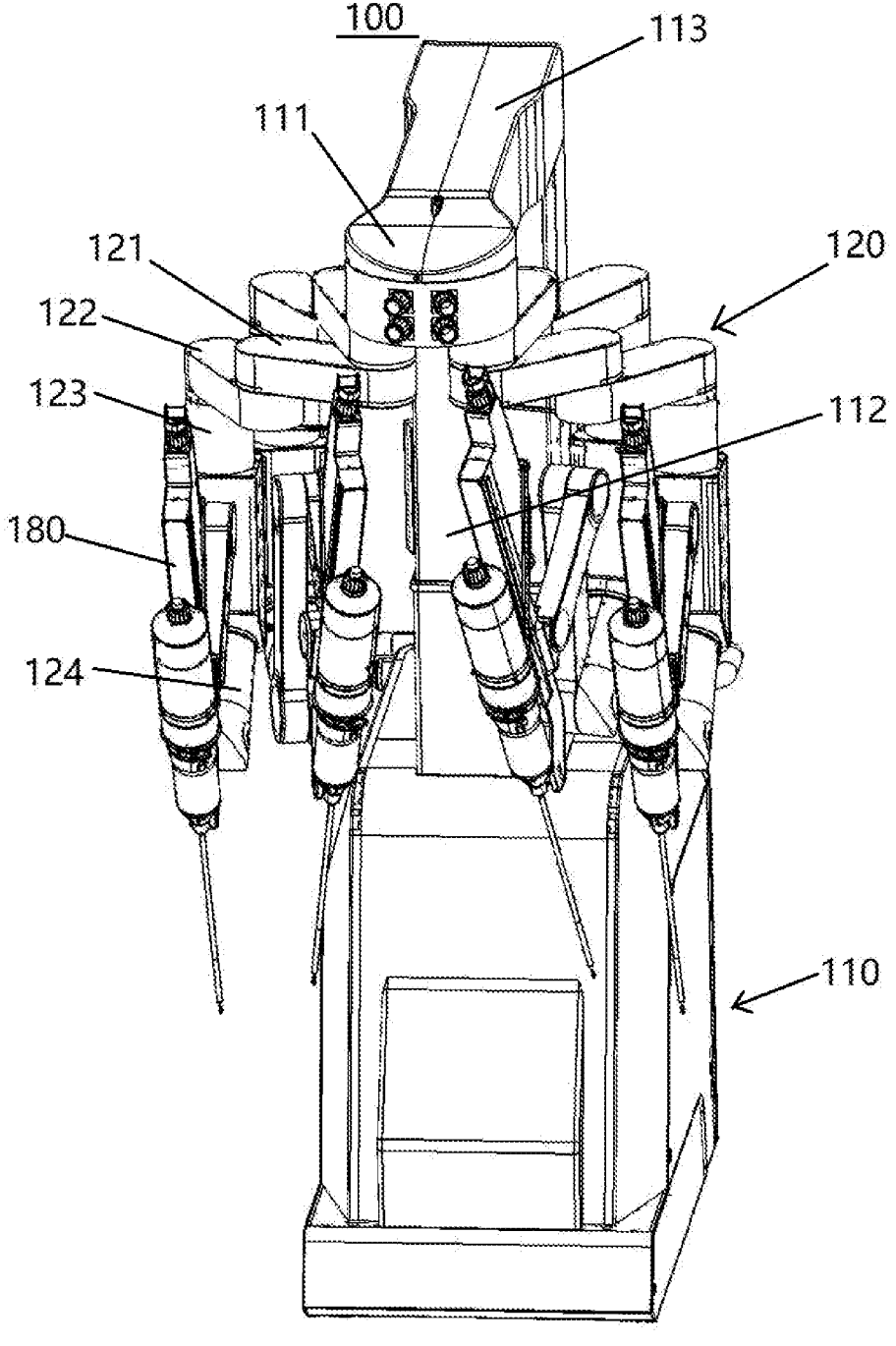
FIG. 1 shows a schematic structural diagram of a surgical robot system according to some embodiments of the present disclosure.

FIG. 1 shows a schematic structural diagram of a surgical robot system 100 according to some embodiments of the present disclosure, and FIG. 2 shows a schematic structural diagram of a positioning arm 120 according to some embodiments of the present disclosure. As shown in FIG. 1, the surgical robot system 100 may comprise at least one surgical cart 110 and at least one positioning arm 120. The at least one surgical cart 110 may comprise a platform 111, It should be understood that in some embodiments, the surgical robot system 100 may not comprise the surgical cart 110, and the platform 111 may be mounted on another structure, such as a support or a building. As shown in FIGS. 1 and 2, the at least one positioning arm 120 (e.g., a positioning arm 120a or a positioning arm 120b of FIG. 2) may comprise a first cross arm 121 (e.g., a first cross arm 121a or a first cross arm 121b of FIG. 2) and a first rotary joint (e.g., a first rotary joint 130 or a first rotary joint 140 of FIG. 2). The first rotary joint may be arranged in the first cross arm 121 or in the platform 111. A proximal end of the first cross arm 121 is rotatably connected to the platform 111 via the first rotary joint, so that the first cross arm 121 rotates about a rotation axis of the first rotary joint (e.g., an axis perpendicular to a horizontal plane) relative to the platform 111. It should be understood that the rotation axis of the first rotary joint may be arranged in a longitudinal direction, which is a height direction of the surgical cart 110. In some embodiments, the surgical cart 110 may further comprise a cart base 112 and a cross beam 113 mounted on top of the cart base 112. The platform 111 may be fixedly arranged at an end of the cross beam 113, and configured to support the at least one positioning arm 120. In some embodiments, the cross beam 113 may be perpendicular to a height direction of the cart base 112. It should be understood that although four positioning arms 120 are shown in FIG. 1, the surgical robot system 100 may comprise another number of positioning arms 120, such as one, two, or five.

Figure 5:
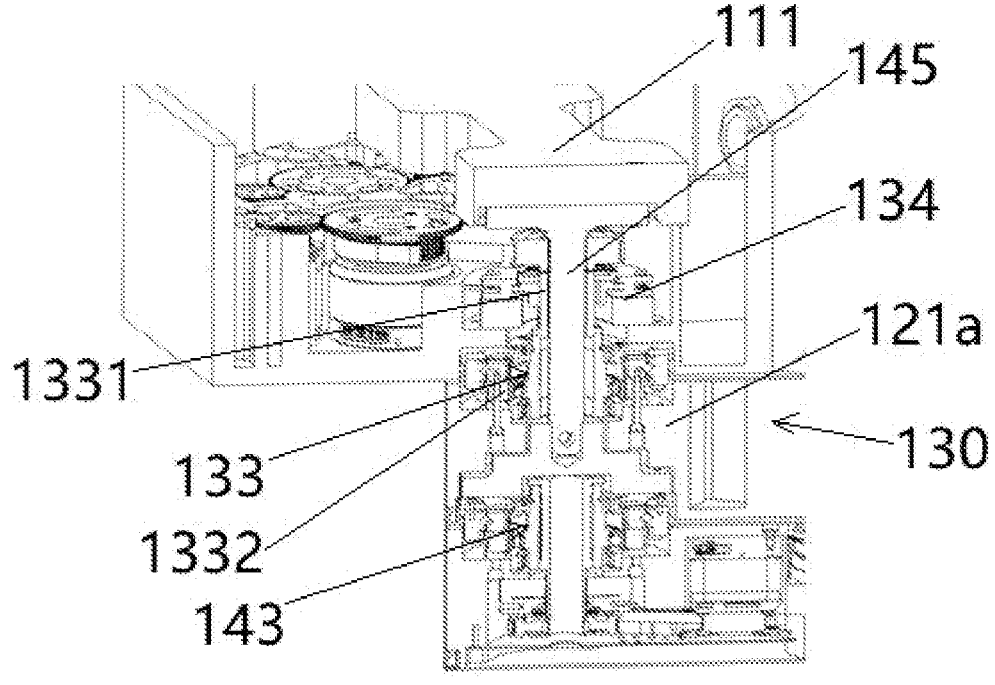
FIG. 5 shows a longitudinal partial cross-sectional view of a first rotary joint of a first positioning arm according to some embodiments of the present disclosure.

In some embodiments, as shown in FIG. 2, the at least one positioning arm 120 may comprise a first positioning arm 120a and a second positioning arm 120b. A first cross arm 121a of the first positioning arm 120a and a first cross arm 121b of the second positioning arm 120b are rotatable relative to each other. A proximal end of the first cross arm 121a of the first positioning arm 120a and a proximal end of the first cross arm 121b of the second positioning arm 120b are separately rotatably connected to the platform 111. In some embodiments, as shown in FIG. 2, a rotation axis of the first rotary joint 130 of the first positioning arm 120a is arranged coaxially with a rotation axis of the first rotary joint 140 of the second positioning arm 120b. The first cross arm 121a of the first positioning arm 120a may partially overlap the first cross arm 121b of the second positioning arm 120b in the longitudinal direction. In this way, the first positioning arm 120a and the second positioning arm 120b may form a group of partially overlapped positioning arms, which can significantly reduce the size of the positioning arms in a transverse space and increase a movement space thereof. In addition, swing interference of the first cross arms 120a-b of the first positioning arm 120a and the second positioning arm 120b in a horizontal plane can be avoided, FIG. 3 shows a schematic structural diagram of a platform 111 according to some embodiments of the present disclosure. FIGS. 4 and 5 are a partial schematic diagram and a longitudinal partial cross-sectional view of a first rotary joint 130 of a first positioning arm 120a according to some embodiments of the present disclosure, respectively. In some embodiments, as shown in FIGS. 3 to 5, the first rotary joint 130 of the first positioning arm 120a may comprise a first electric motor 131, a first transmission device 132, and a first speed reducer 133. The first electric motor 131 may be fixedly arranged in the platform 111, and the first transmission device 132 is linked with the first electric motor 131, and is configured to transmit a driving force of the first electric motor 131. As shown in FIGS. 4 and 5, the first speed reducer 133 may comprise a first speed reducer input shaft 1331 and a first speed reducer output shaft 1332. The first speed reducer input shaft 1331 is connected to an output shaft of the first electric motor 131 via the first transmission device 132. The first speed reducer output shaft 1332 is fixedly connected to the first cross arm 121a of the first positioning arm 120a, and is configured to drive the first cross arm 121a of the first positioning arm 120a to rotate. In some embodiments, a housing of the first speed reducer 133 is fixedly arranged in the platform 111, and the first speed reducer output shaft 1332 and the first speed reducer input shaft 1331 can rotate relative to the housing thereof. The first speed reducer output shaft 1332 is fixedly connected to the first cross arm 121a of the first positioning arm 120a via fasteners (e.g., a group of bolts), so as to drive the first cross arm 121a of the first positioning arm 120a to rotate. In some embodiments, the first speed reducer 133 may be a harmonic speed reducer.

In some embodiments, as shown in FIG. 4, the first transmission device 132 may comprise a first pulley 1321 and a first synchronous transmission belt 1322. The first pulley 1321 and the output shaft of the first electric motor 131 are coaxially and fixedly arranged. A transmission wheel matching the first pulley 1321 is coaxially and fixedly arranged on the first speed reducer input shaft 1331, and the first synchronous transmission belt 1322 is wound around the first pulley 1321 and the transmission wheel. In this way, the output shaft of the first electric motor 131 drives the rotation of the first speed reducer input shaft 1331 by means of the first synchronous transmission belt 1322, so as to form rotational motion of the first speed reducer input shaft 1331, The rotation of the first speed reducer input shaft 1331 may be converted, through speed reduction transmission of the first speed reducer 133, to an output torque of the first speed reducer output shaft 1332 at a lower speed, which a proportionally increased torque, so as to drive the first cross arm 121a of the first positioning arm 120a to perform relative rotational movement around the first speed reducer output shaft 1332 relative to the platform 111, thereby forming the first rotary joint 130 of the first positioning arm 120a. It should be understood that the first synchronous transmission belt 1322 may be a rubber belt or a chain belt. In some embodiments, the first transmission device 132 may further comprise another structure capable of implementing motion transmission, such as a gear transmission structure.

In some embodiments, as shown in FIGS. 4 and 5, the first rotary joint 130 of the first positioning arm 120a may further comprise a first contracting brake 134 arranged coaxially with the first speed reducer input shaft 1331. The first contracting brake 134 may be located between the transmission wheel and the first speed reducer output shaft 1332. Under a power-on condition, the first contracting brake 134 is in an operating state (e.g., an unlocked state), so that a driving force of the first electric motor 131 is transmitted to the first speed reducer input shaft 1331 through the first synchronous transmission belt 1322, thereby driving the first cross arm of the first positioning arm 120a to move. Under a power-off condition, the first contracting brake 134 is in a closed state (e.g., a locked state), so that the driving force of the first electric motor 131 cannot be transmitted to the first speed reducer 133 or the first positioning arm 120*a*, and the first positioning arm 120*a* is locked. Therefore, the safety of the first rotary joint 130 can be improved to avoid injury caused by accidental movement of the positioning arm.

In some embodiments, as shown in FIG. 4, the first rotary joint 130 of the first positioning arm 120*a* may further comprise a first gear 135 and a first angle encoder 136. The first gear 135 and the output shaft of the first electric motor 131 are coaxially and fixedly arranged, and the first angle encoder 136 meshes with the first gear 135. Rotational movement output by the first electric motor 131 is transmitted to the first angle encoder 136 through the first gear 135. With the first angle encoder 136, angular displacement information of the first electric motor 131 can be monitored in real time, so that a motion state of the first rotary joint 130 of the first positioning arm 120*a* is recorded and fed back. In some embodiments, the first gear 135 may be further coaxially and fixedly arranged on the first speed reducer input shaft 1331. It should be understood that synchronous movement between the first gear 135 and the first angle encoder 136 may also be implemented through a pulley, so that angular displacement information of the first electric motor 131 is monitored by the first angle encoder 136. In some embodiments, the first angle encoder 136 may alternatively be a potentiometer, or another device that can detect angular displacement.

Figure 6:
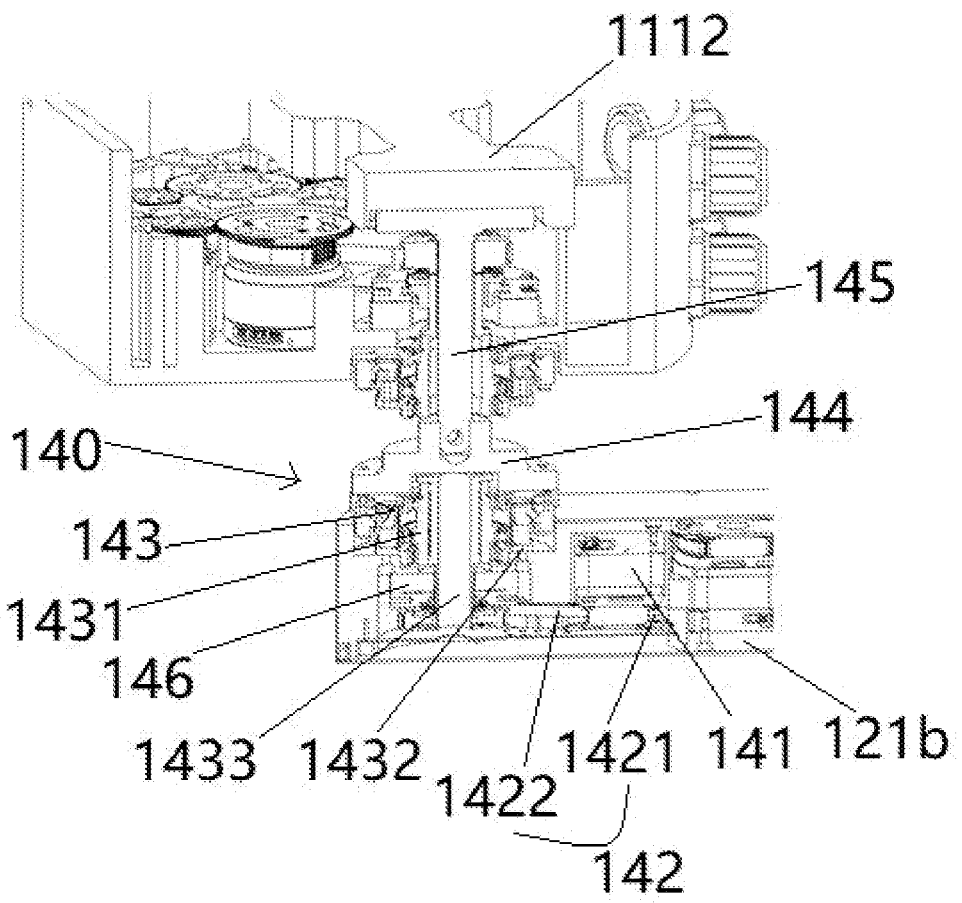
FIG. 6 shows a longitudinal partial cross-sectional view of a first rotary joint of a second positioning arm according to some embodiments of the present disclosure.

FIG. 6 is a longitudinal partial cross-sectional view of a first rotary joint 140 of a second positioning arm 120*b* according to some embodiments of the present disclosure. In some embodiments, as shown in FIG. 6, the first rotary joint 140 of the second positioning arm 120*b* may comprise a second electric motor 141, a second transmission device 142, a speed reducer base 144, a support shaft 145, and a second speed reducer 143. The second electric motor 141 and the speed reducer base 144 may be fixedly arranged in the first cross arm 121*b* of the second positioning arm 120*b*. The second transmission device 142 is linked with the second electric motor 141, and is configured to transmit a driving force of the second electric motor 141. A proximal end of the support shaft 145 passes through the first speed reducer 133 and the first speed reducer input shaft 1331, and is fixedly connected to the platform 111. A distal end of the support shaft 145 is fixedly connected to the speed reducer base 144. In some embodiments, as shown in FIG. 6, the second speed reducer 143 may comprise a second speed reducer transmission shaft 1433, a second speed reducer input shaft 1431, and a second speed reducer output shaft 1432. A proximal part of the second speed reducer 143 is fixedly connected to the speed reducer base 144, and a proximal end of the second speed reducer transmission shaft 1433 passes through the second speed reducer 143 from the second speed reducer output shaft 1432 located at the distal end, and is coaxially and fixedly connected to the second speed reducer input shaft 1431 located at the proximal end. A distal end of the second speed reducer transmission shaft 1433 is connected to an output shaft of the second electric motor 141 via the second transmission device 142. The second speed reducer output shaft 1432 is fixedly connected to the first cross arm 121*b* of the second positioning arm 120*b*, and is configured to drive the first cross arm 121*b* of the second positioning arm 120*b* to rotate. In some embodiments, a housing of the second speed reducer 143 is fixedly arranged in the speed reducer base 144, and the second speed reducer output shaft 1432 and the second speed reducer input shaft 1431 can rotate relative to the housing thereof. The second speed reducer output shaft 1432 is fixedly connected to the first cross arm 121*b* of the second positioning arm 120*b* via fasteners (e.g., a group of bolts), thereby driving the first cross arm 121*b* of the second positioning arm 120*b* to rotate. In some embodiments, the second speed reducer 143 may be a harmonic speed reducer.

In some embodiments, as shown in FIG. 6, the second transmission device 142 may comprise a second pulley 1421 and a second synchronous transmission belt 1422. The second pulley 1421 and the output shaft of the second electric motor 141 are coaxially and fixedly arranged. A transmission wheel matching the second pulley 1421 is coaxially and fixedly arranged on the second speed reducer transmission shaft 1433, and the second synchronous transmission belt 1422 is wound around the second pulley 1421 and the transmission wheel. In this way, the output shaft of the second electric motor 141 drives the rotation of the second speed reducer transmission shaft 1433 by means of the second synchronous transmission belt 1422, so as to form rotational motion of the second speed reducer input shaft 1431. The rotation of the second speed reducer input shaft 1431 is converted, through speed reduction transmission of the second speed reducer 143, to an output torque of the second speed reducer output shaft 1432 at a lower speed, which is a proportionally increased torque, so as to relatively rotate the second speed reducer output shaft 1432 with respect to the speed reducer base 144, so that relative rotational motion is generated between the first cross arm 121*b* of the second positioning arm 120*b* and the platform 111, thereby forming the first rotary joint 140 of the second positioning arm 120*b*. It should be understood that the second synchronous transmission belt 1422 may be a rubber belt or a chain belt. In some embodiments, the second transmission device 142 may further comprise another structure capable of implementing motion transmission, such as a gear transmission structure.

In some embodiments, as shown in FIGS. 5 and 6, the first speed reducer 133 and the first speed reducer input shaft 1331 may comprise a through channel along a central axis of rotation. In some embodiments, the support shaft 145 passes through the through channel and is fixedly connected to the speed reducer base 144 to connect the first cross arm 121*b* of the second positioning arm 120*b* to the platform 111, so that the first cross arms 121*a-b* of the first positioning arm 120*a* and the second positioning arm 120*b* are connected to the platform 111 independently of each other. The first speed reducer input shaft 1331 and the first speed reducer 133 are of a hollow design, so that the support shaft 145 passes through the first speed reducer input shaft 1331 and the first speed reducer 133 and is connected to the second positioning arm 120*b*, without being affected by the movement of the first positioning arm 120*a*. In some embodiments, as shown in FIG. 3, the platform 111 may comprise a platform frame 1111 and a support shaft base 1112. The support shaft base 1112 is fixedly connected in the platform frame 1111. The proximal end of the support shaft 145 is fixedly arranged on the support shaft base 1112. The first cross arm 121*a* of the first positioning arm 120*a* is connected to the platform frame 1111 via the first rotary joint 130 of the first positioning arm 120*a*. The first cross arm 121*b* of the second positioning arm 120*b* is connected to the support shaft base 1112 via the first rotary joint 140 of the second positioning arm 120*b*.

In some embodiments, as shown in FIG. 6, the first rotary joint 140 of the second positioning arm 120*b* may further comprise a second contracting brake 146 arranged coaxially on the second speed reducer transmission shaft 1433. The second contracting brake 146 may be located between the second synchronous transmission belt 1422 and the second speed reducer output shaft 1432. Under a power-on condition, the second contracting brake 146 is in an operating state (e.g., an unlocked state). In this case, a driving force of the second electric motor 141 is transmitted to the second speed reducer transmission shaft 1433 through the second synchronous transmission belt 1422, and is then transmitted to the second speed reducer input shaft 1431, thereby driving the first cross arm 121b of the second positioning arm 120b to move. Under a power-off condition, the second contracting brake 146 is in a closed state (e.g., a locked state). In this case, the driving force of the second electric motor 141 cannot be transmitted to the second speed reducer 143 or the first cross arm 121b, and the first cross arm 121b of the second positioning arm 120b is locked. In this way, the safety of the first rotary joint 140 can be improved to avoid injury caused by accidental movement of the positioning arm.

In some embodiments, the first rotary joint 140 of the second positioning arm 120b may further comprise a second gear and a second angle encoder (not shown in the figures). The second gear is coaxially and fixedly connected to the output shaft of the second electric motor, and the second angle encoder meshes with the second gear. Rotational motion output by the second electric motor drives the second angle encoder by means of the second gear, and the second angle encoder then monitors angular displacement information of the second electric motor 141 in real time, so that a motion state of the first rotary joint 140 of the second positioning arm 120b is recorded and fed back. In some embodiments, the second gear may be further coaxially and fixedly arranged on the second speed reducer transmission shaft 1433. It should be understood that synchronous movement between the first gear and the first angle encoder may also be implemented through a pulley, so that the angular displacement information of the second electric motor 141 is monitored by the second angle encoder.

Figure 7:
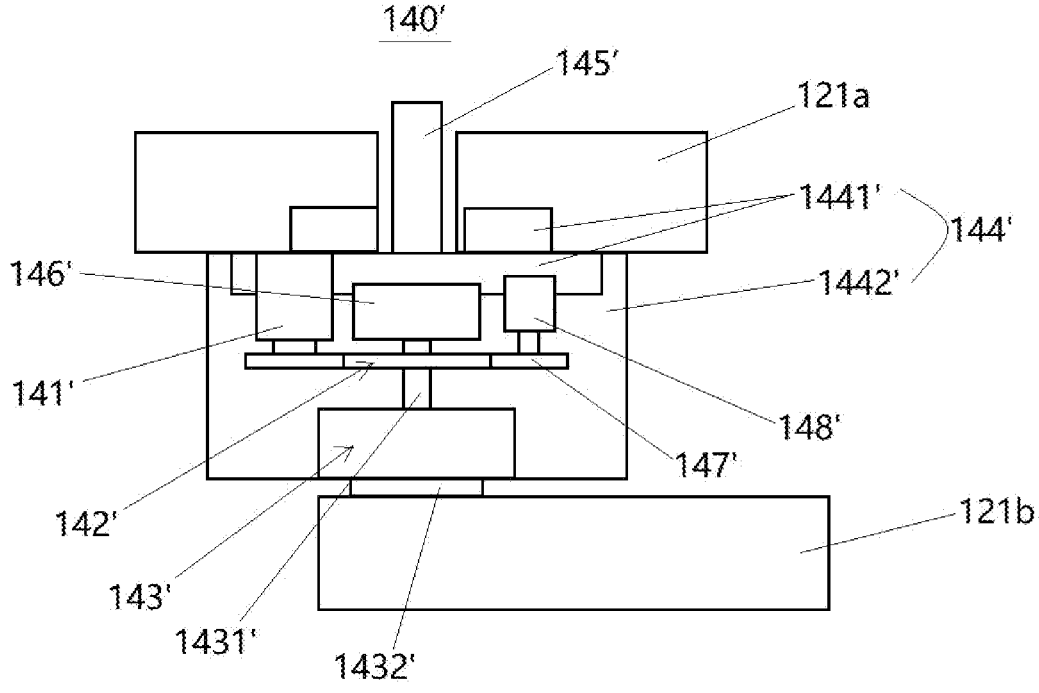
FIG. 7 shows a longitudinal partial cross-sectional schematic diagram of another first rotary joint of a second positioning arm according to some embodiments of the present disclosure.

FIG. 7 is a longitudinal partial cross-sectional schematic diagram of another first rotary joint of a second positioning arm according to some embodiments of the present disclosure. In some embodiments, as shown in FIG. 7, a first rotary joint 140' of the second positioning arm 120b may comprise a driving module seat 144', a support shaft 145', a second electric motor 141', a second transmission device 142', and a second speed reducer 143'. The driving module seat 144' may comprise a base 1441' at least partially arranged in the first cross arm 121a of the first positioning arm 120a and a main body 1442' located at a distal end of the base 1441' and provided with a receiving cavity. A proximal end of the support shaft 145' passes through the first speed reducer 133 and the first speed reducer input shaft 1331, and is fixedly connected to the platform 111, and a distal end thereof is fixedly connected to the base 1441'. The second electric motor 141' is fixedly arranged in the main body 1442', and the second transmission device 142' is linked with the second electric motor 141', and is configured to transmit a driving force of the second electric motor 141'. The second speed reducer 143' may comprise a second speed reducer input shaft 1431' and a second speed reducer output shaft 1432'. The second speed reducer 143' is fixedly arranged in the main body 1442', and the second speed reducer input shaft 1431' is connected to an output shaft of the second electric motor 141' via the second transmission device 142'. The second speed reducer output shaft 1432' is fixedly connected to the first cross arm 121b of the second positioning arm 120b, and is configured to drive the first cross arm 121b of the second positioning arm 120b to rotate. In some embodiments, the second speed reducer 143' may be a harmonic speed reducer. In some embodiments, a housing of the second speed reducer 143' is fixedly arranged in the main body 1442', and the second speed reducer output shaft 1432' and the second speed reducer input shaft 1431' can rotate relative to the housing thereof. The second speed reducer output shaft 1432' is fixedly connected to the first cross arm 121b of the second positioning arm 120b via fasteners (e.g., a group of bolts), so as to drive the first cross arm 121b of the second positioning arm 120b to rotate. In some embodiments, the second transmission device 142' may comprise a second pulley and a second synchronous transmission belt (not shown in the figures), the second pulley and the output shaft of the second electric motor 141' are coaxially and fixedly arranged, a transmission wheel matching the pulley is coaxially and fixedly arranged on the second speed reducer input shaft 1431', and the second synchronous transmission belt is wound around the second pulley and the transmission wheel. In this way, the output shaft of the second electric motor 141' drives the rotation of the second speed reducer input shaft 1431' by means of the second synchronous transmission belt, thereby driving the first cross arm 121b of the second positioning arm 120b and the platform 111 to generate relative rotational motion.

In some embodiments, as shown in FIG. 7, the first rotary joint 140' of the second positioning arm 120b may further comprise a second angle encoder 148' and a second contracting brake 146'. The second contracting brake 146' is arranged coaxially with the second speed reducer input shaft 1431', and the second angle encoder 148' may move synchronously with the output shaft of the second electric motor 141' by means of a second gear 147'. It should be understood that the second angle encoder 148' may also move synchronously with the output shaft of the second electric motor by means of a synchronous belt, and the second angle encoder 148' then monitors angular displacement information of the second electric motor 141' in real time, so that a motion state of the first rotary joint 140' of the second positioning arm 120b is recorded and fed back.

In some embodiments, as shown in FIGS. 1 and 2, the first positioning arm 120a (or the second positioning arm 120b) may further comprise at least one second cross arm 122 and a second rotary joint 150. A proximal end of the at least one second cross arm 122 is rotatably connected to a distal end of the first cross arm 121a via the second rotary joint 150, so that the second cross arm 122 rotates about the longitudinal axis relative to the first cross arm 121a. In some embodiments, the distal end of the first cross arm 121a is arranged overlapping a proximal end portion of the second cross arm 122. The distal end of the first cross arm 121a is located above the proximal end of the second cross arm 122, and rotation axes of the first cross arm 121a and the second cross arm 122 are parallel in the longitudinal direction. With the first rotary joint 130 and the second rotary joint 150, a transverse space of the positioning arm can be reduced without affecting the transverse deployment movement of the positioning arm in the space, so that a bedside space and a working space of the positioning arm can be used more efficiently.

In some embodiments, the first positioning arm 120a (or the second positioning arm 120b) may further comprise a plurality of second cross arms 122 and a plurality of second rotary joints 150. Each of the second cross arms 122 comprises a proximal end portion and a distal end portion, and the plurality of second cross arms 122 are connected end to end at each proximal end portion and each distal end portion respectively via corresponding second rotary joints 150, and two adjacent second cross arms 122 can rotate about the longitudinal axis relative to each other.

In some embodiments, as shown in FIGS. 1 and 2, the first positioning arm 120*a* (or the second positioning arm 120*b*) may further comprise a vertical arm 123 and a vertical arm rotary joint 160. In some embodiments, the vertical arm 123 may comprise a vertical arm outer cylinder 1231 and a vertical arm inner cylinder 1232 which are movable relative to each other in the direction of the longitudinal axis. One of the vertical arm outer cylinder 1231 and the vertical arm inner cylinder 1232 is connected to a distal end of the second cross arm 122 via the vertical arm rotary joint 160, to rotate about the longitudinal axis relative to the distal end of the second cross arm 122. In some embodiments, the vertical arm inner cylinder 1232 is connected to a lower portion of the distal end portion of the second cross arm 122 via the vertical arm rotary joint 160. In some embodiments, a driving electric motor or a motor (not shown in the figures) may be provided in the vertical arm inner cylinder 1232. An output end of the electric motor or the motor is fixedly connected to a motion conversion mechanism, and an output end of the motion conversion mechanism is fixedly connected to the vertical arm outer cylinder 1231. It should be understood that the motion conversion mechanism may comprise a structure for converting rotational motion into linear motion, such as a lead screw-nut structure. When the electric motor or the motor operates, the motion conversion mechanism converts rotational motion of the electric motor or the motor into linear motion, thereby driving the vertical arm outer cylinder 1231 to move up and down, so as to implement relative movement between the vertical arm outer cylinder 1231 and the vertical arm inner cylinder 1232. In some embodiments, the vertical arm outer cylinder 1231 may alternatively be connected to a lower portion of the distal end portion of the second cross arm 122 via the vertical arm rotary joint 160, and the driving electric motor or the motor drives the vertical arm inner cylinder 1232 to move up and down, so as to implement relative movement between the vertical arm outer cylinder 1231 and the vertical arm inner cylinder 1232.

In some embodiments, as shown in FIGS. 1 and 2, the first positioning arm 120*a* (or the second positioning arm 120*b*) may further comprise an inclined arm 124 and an inclined arm rotary joint 170. A proximal end of the inclined arm 124 may be connected to the vertical arm outer cylinder 1231 via the inclined arm rotary joint 170, and a rotation axis of the inclined arm rotary joint 170 is at an angle with a rotation axis of the vertical arm rotary joint 160. In some embodiments, the rotation axis of the vertical arm rotary joint 160 is in the longitudinal direction, and there is an included angle between the rotation axis of the inclined arm rotary joint 170 and the rotation axis of the vertical arm rotary joint 160, so that the inclined arm 124 performs deflection motion relative to the vertical arm 123. It should be understood that the included angle between the rotation axis of the inclined arm rotary joint 170 and the rotation axis of the vertical arm rotary joint 160 may be between 0° and 90°. In some embodiments, the included angle between the rotation axis of the inclined arm rotary joint 170 and the rotation axis of the vertical arm rotary joint 160 is 45°.

The first cross arm 121*a* and the second cross arm 122 of the first positioning arm 120*a* (or the second positioning arm 120*b*) can be driven to perform rotational motion in the transverse direction (e.g., in the horizontal direction) by means of the first rotary joint 130 and the second rotary joint

150, thereby implementing transverse position adjustment of the first positioning arm 120*a*. The vertical arm 123 of the first positioning arm 120*a* (or the second positioning arm 120*b*) can be driven to move in the longitudinal direction by means of the vertical arm rotary joint 160, so as to implement vertical position adjustment of the first positioning arm 120*a*. The inclined arm 124 of the first positioning arm 120*a* (or the second positioning arm 120*b*) can be driven to perform lateral rotational motion by means of the inclined arm rotary joint 170, so as to implement lateral swing position adjustment of the first positioning arm 120*a*. The foregoing joints can implement in-vitro positioning of the positioning arm to meet requirements of preoperative or intraoperative position adjustment, thereby facilitating a surgical operation.

Figure 8:
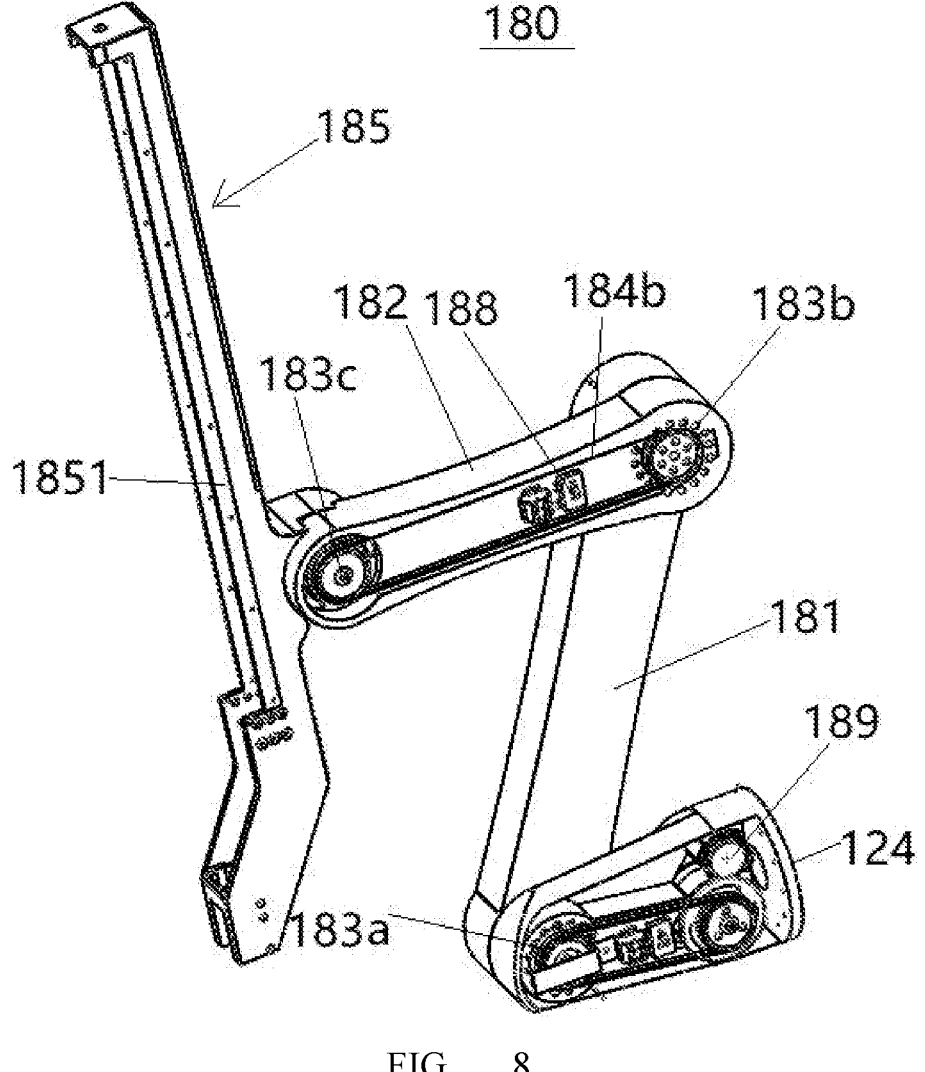
FIG. 8 shows a perspective view of a remote center motion mechanism according to some embodiments of the present disclosure.
Figure 9:
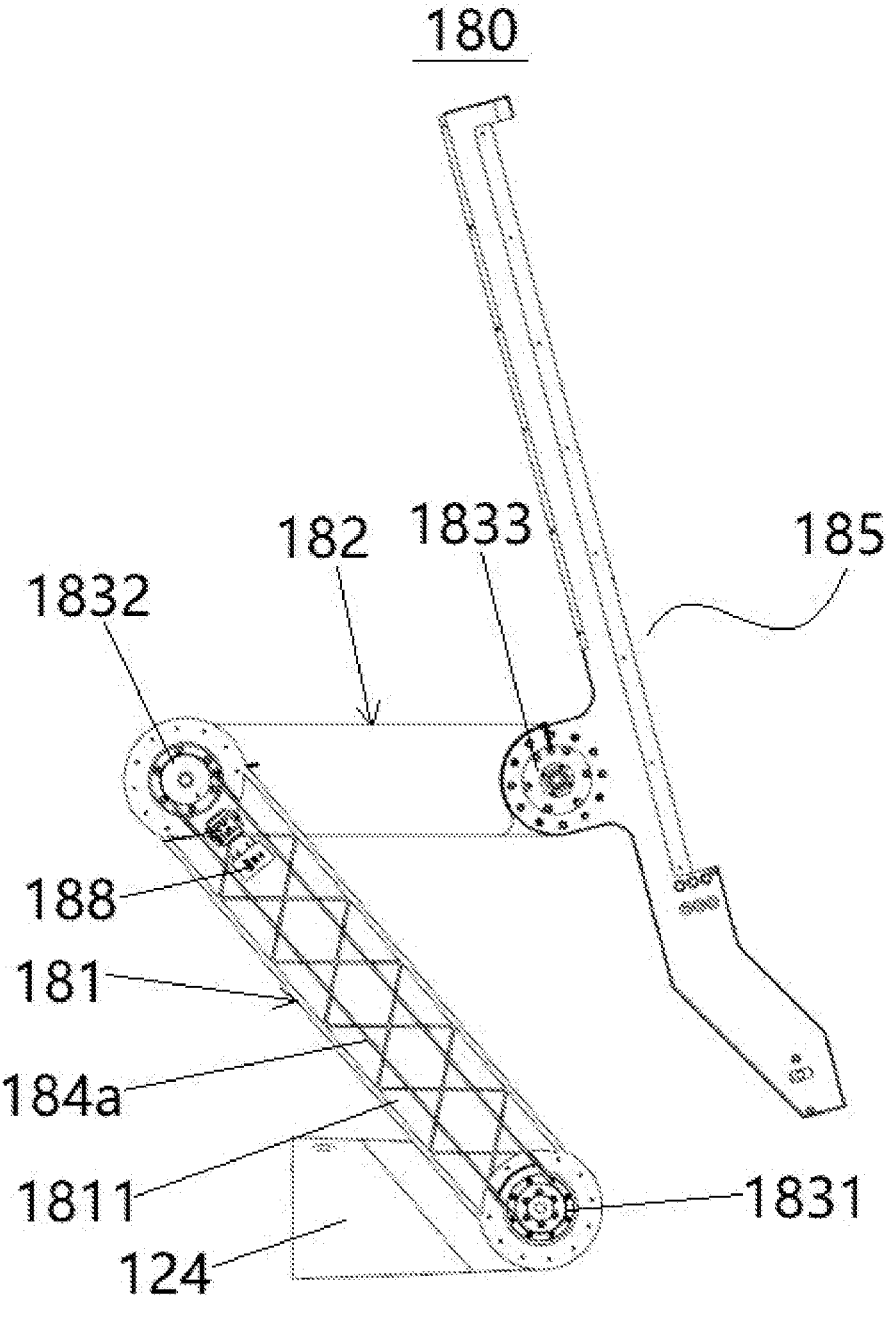
FIG. 9 shows a front view of a remote center motion mechanism according to some embodiments of the present disclosure.

In some embodiments, the first positioning arm 120*a* (or the second positioning arm 120*b*) may further comprise a remote center motion mechanism. FIGS. 8, 9 and 10 are respectively a perspective view, a front view, and a rear view of a remote center motion mechanism 180 according to some embodiments of the present disclosure. In some embodiments, as shown in FIGS. 8 to 10, the remote center motion mechanism 180 may comprise a first movable arm 181, a first movable joint 183*a*, a second movable arm 182, a second movable joint 183*b*, a third movable joint 183*c*, a first transmission mechanism, a second transmission mechanism, and a third movable arm 185. The first movable joint 183*a* may be arranged in the first movable arm 181 or the inclined arm 124, and a proximal end of the first movable arm 181 is rotatably connected to a distal end of the inclined arm 124 via the first movable joint 183*a*. The second movable joint 183*b* may be arranged in the first movable arm 181 or the second movable arm 182, and a distal end of the first movable arm 181 is rotatably connected to a proximal end of the second movable arm 182 via the second movable joint 183*b*. The third movable joint 183*c* may be arranged in the second movable arm 182 or the third movable arm 185. The first transmission mechanism is connected to the first movable joint 183*a* and the second movable joint 183*b*, so that the first movable joint 183*a* is linked with the second movable joint 183*b*. The second transmission mechanism is connected to the second movable joint 183*b* and the third movable joint 183*c*, so that the second movable joint 183*b* is linked with the third movable joint 183*c*.

The third movable arm 185 is rotatably connected to a distal end of the second movable arm 182 via the third movable joint 183*c*, so that a distal end of the third movable arm 185 moves around a remote center point. In some embodiments, the third movable arm 185 may be an instrument connecting portion, and is configured to connect a surgical instrument. It should be understood that the remote center point may be a remote center of motion (RCM), such as an abdominal entry point where a sheath and the surgical instrument are inserted. A distal end of the remote center motion mechanism 180 may always perform rotational motion around the remote center of motion, so as to implement a rotation operation on a fixed point near a surgical site of a patient.

In some embodiments, as shown in FIGS. 9 and 10, the first movable joint 183*a* may comprise a first speed reduction wheel 1831. The first speed reduction wheel 1831 may comprise a first input shaft and a first output shaft which can rotate relative to each other. The first speed reduction wheel 1831 may be located at the proximal end of the first movable arm 181. The first input shaft is driven by a driving device, such as an electric motor, to rotate, and drives the first output shaft to rotate through speed reduction transmission of the first speed reduction wheel 1831. The first output shaft is fixedly connected to the first movable arm 181, and is configured to drive the first movable arm 181 to rotate to form the first movable joint 183*a*. The second movable joint 183*b* may comprise a second speed reduction wheel 1832. The second speed reduction wheel 1832 may comprise a second input shaft and a second output shaft which can rotate relative to each other. The second speed reduction wheel 1832 may be located at the distal end of the first movable arm 181 and the proximal end of the second movable arm 182. The second input shaft is driven by a driving device, such as an electric motor, to rotate, and drives the second output shaft to rotate through speed reduction transmission of the second speed reduction wheel 1832. The second output shaft is fixedly connected to the second movable arm 182 or the first movable arm 181, and is configured to drive the second movable arm 182 or the first movable arm 181 to rotate to form the second movable joint 183*b*. The third movable joint 183*c* may comprise a third speed reduction wheel 1833. The third speed reduction wheel 1833 may comprise a third input shaft and a third output shaft which can rotate relative to each other. The third speed reduction wheel 1833 may be located at the distal end of the second movable arm 182. The third input shaft is driven by a driving device, such as an electric motor, to rotate, and drives the third output shaft to rotate through speed reduction transmission of the third speed reduction wheel 1833. The third output shaft is fixedly connected to the third movable arm 185, and is configured to drive the third movable arm 185 to rotate to form the third movable joint 183*c*. The first transmission mechanism may comprise a first transmission belt 184*a*, and the second transmission mechanism may comprise a second transmission belt 184*b*. The first transmission belt 184*a* is wound around the first input shaft and the second input shaft, and the second transmission belt 184*b* is wound around the second input shaft and the third input shaft, to implement linkage of the first input shaft, the second input shaft and the third input shaft by means of the driving device. In some embodiments, transmission wheels may be coaxially and fixedly arranged on the first input shaft, the second input shaft, and the third input shaft respectively, and the first transmission belt 184*a* and the second transmission belt 184*b* may be wound around the input shafts with the corresponding transmission wheels. In some embodiments, the first transmission belt 184*a* and the second transmission belt 184*b* each may comprise various transmission chains, flexible synchronous belts, rigid synchronous belts, etc.

In some embodiments, rotation axes of the first movable joint 183*a*, the second movable joint 183*b* and the third movable joint 183*c* are parallel to one another, and planes in which the first movable joint 183*a*, the second movable joint 183*b* and the third movable joint 183*c* are located are perpendicular to the rotation axes. In this way, the first movable arm 181 and the second movable arm 182 form an RCM mechanism equivalent to a double parallelogram structure by means of the first transmission belt 184*a* and the second transmission belt 184*b*, so that the distal end of the third movable arm 185 mounted at the distal end of the second movable arm 182 moves around the remote center point. In some embodiments, the first speed reduction wheel 1831, the second speed reduction wheel 1832 and the third speed reduction wheel 1833 may be harmonic speed reducers.

In some embodiments, as shown in FIG. 10, the surgical robot system 100 may further comprise an auxiliary power mechanism. The auxiliary power mechanism may comprise a third electric motor 186 and a third pulley 187. The third electric motor 186 and the third pulley 187 are arranged in the inclined arm, and the third pulley 187 is coaxially and fixedly connected to an output shaft of the third electric motor 186, The third transmission device may comprise a third transmission belt 184*c*. A proximal end of the third transmission belt 184*c* surrounds the third pulley 187, and a distal end thereof surrounds the first input shaft to transmit power from the third electric motor 186 to the first input shaft. In some embodiments, the third transmission belt 184*c* may comprise various transmission chains, flexible synchronous belts, rigid synchronous belts, etc. In some embodiments, the transmission belts may be connected to the pulleys or the transmission wheels by meshing teeth with grooves. The third electric motor 186 drives the third pulley 187 to rotate, so that the third transmission belt 184*c* connected to the third pulley 187 moves synchronously, and drives the first input shaft of the first speed reduction wheel 1831 connected to the third transmission belt 184*c* to rotate. A certain multiple of the driving force from the first input shaft is output to drive the first output shaft of the first speed reduction wheel 1831 to rotate, so as to create rotation of the first movable joint 183*a*. The first input shaft drives the second input shaft of the second speed reduction wheel 1832 to rotate synchronously by means of the first transmission belt 184*a*. A certain multiple of the driving force from the second input shaft is output to drive the second output shaft of the second speed reduction wheel 1832 to rotate, so as to create rotation of the second movable joint 183*b*. The second input shaft drives the third input shaft of the third speed reduction wheel 1833 to rotate synchronously by means of the second transmission belt 184*b*. A certain multiple of the driving force from the third input shaft is output to drive the third output shaft of the third speed reduction wheel 1833 to rotate, so as to create rotation of the third movable joint 183*c*. In this way, the third movable arm 185 can be controlled to rotate about the third movable joint 183*c*. Rotational angular velocities of the first output shaft, the second output shaft and the third output shaft may be the same. In some embodiments, the first speed reduction wheel 1831, the second speed reduction wheel 1832 and the third speed reduction wheel 1833 may have the same speed reduction ratio to control the angular velocity of each output shaft to be the same. In some embodiments, the first speed reduction wheel 1831, the second speed reduction wheel 1832 and the third speed reduction wheel 1833 may have different speed reduction ratios, and the angular velocity of each output shaft can be the same by changing the radius of a corresponding pulley or transmission wheel. The auxiliary power mechanism can drive the first movable arm 181 with auxiliary power, and movement and attitude data of the first movable arm 181 may be obtained by detecting a rotation speed of the third electric motor 186 and monitoring a state thereof.

In some embodiments, as shown in FIGS. 8 to 10, the remote center motion mechanism 180 further comprises at least one brake mechanism 188 and at least one angle encoder 189 (or potentiometer). The at least one brake mechanism 188 is coupled to (e.g., arranged coaxially with or coupled, via a transmission device, to) the first speed reduction wheel 1831, the second speed reduction wheel 1832 or the third speed reduction wheel 1833. The at least one brake mechanism 188 may be disposed to brake in a power-off state to lock a corresponding speed reduction wheel, and release in a power-on state to unlock the corresponding speed reduction wheel. In some embodiments, three brake mechanisms 188 may be coupled to the first speed reduction wheel 1831, the second speed reduction wheel 1832 and the third speed reduction wheel 1833 respectively, and are configured to lock or release the corresponding speed reduction wheels. The at least one angle encoder 189 (or potentiometer) is arranged on the corresponding first speed reduction wheel 1831, second speed reduction wheel 1832, and third speed reduction wheel 1833, or is arranged on the corresponding pulleys or transmission wheels. For example, the at least one angle encoder (or potentiometer) may be connected by means of gear meshing, and is configured to record and feed back a motion state of the remote center motion mechanism 180. In some embodiments, the brake mechanism 188 may be a contracting brake. The brake mechanism 188 is provided to improve the overall stability of the remote center motion mechanism 180.

FIG. 11 is a schematic diagram of a partial structure of a first movable arm 181 according to some embodiments of the present disclosure. In some embodiments, as shown in FIGS. 9 to 11, the first movable arm 181 is provided with a first strip-shaped groove 1811, and the second movable arm 182 is provided with a second strip-shaped groove 1821. The first strip-shaped groove 1811 and the second strip-shaped groove 1821 are respectively located in side faces of the first movable arm 181 and the second movable arm 182 which are away from each other. The first transmission belt 184*a* and the second transmission belt 184*b* are respectively located in the first strip-shaped groove 1811 and the second strip-shaped groove 1821 in a non-contact manner. Reinforcing rib structures may be provided in the first strip-shaped groove 1811 and the second strip-shaped groove 1821. In this way, the overall weight of the remote center motion mechanism 180 can be reduced while the strength is basically the same, and the first transmission belt 184*a* and the second transmission belt 184*b* can be protected. By arranging the reinforcing rib structures in the grooves, the volume of the movable arm can also be effectively reduced when the housing is wrapped.

In some embodiments, as shown in FIGS. 1 and 8, the third movable arm 185 may comprise a linear movement assembly 1851 and a surgical instrument 1852. The linear movement assembly 1851 is arranged in a lengthwise direction of the third movable arm 185, and the surgical instrument 1852 is detachably mounted on the linear movement assembly 1851, and is driven by the linear movement assembly 1851 to move relative to the lengthwise direction of the third movable arm 185. In some embodiments, the surgical instrument 1852 may comprise a surgical tool or an endoscope. An end of the surgical tool is connected to an end surgical effector, and an end of the endoscope tool is connected to a lighting device or an image acquisition device.

In some embodiments, an on/off and/or operation switch of the brake mechanism 188 of the remote center motion mechanism 180 may be arranged on the third movable arm 185. When an operator needs to manually adjust an attitude of the remote center motion mechanism 180, a corresponding on/off and/or operation switch may be pressed and held to power on and release the brake mechanism 188 associated therewith, so that the attitude of the movable arm can be changed. When the on-off and/or operation switch is released, the brake mechanism 188 is powered off and the brake is applied, so that the attitude of the movable arm remains unchanged.

In some embodiments, as shown in FIGS. 1 and 2, the surgical robot system 100 may comprise at least two groups of positioning arms, each group being composed of a first positioning arm 120*a* and a second positioning arm 120*b*. The at least two groups of positioning arms may be in mirror symmetry with respect to a central cross section of the platform 111. A plurality of positioning arms may move relatively independently of one another, swing interference between the positioning arms will not occur, and various surgeries such as a single-port surgery, a multi-port surgery or a mixed-port surgery can be implemented.

In some embodiments of the present disclosure, a first cross arm (e.g., the first cross arm 121 of FIG. 1 or the first cross arm 121*a* or the first cross arm 121*b* of FIG. 2) of a positioning arm is connected to a platform (e.g., the platform 111 of FIG. 1) through a first rotary joint (e.g., the first rotary joint 130 or the first rotary joint 140 of FIG. 2). Furthermore, in some embodiments, first cross arms of a pair of positioning arms may overlap and be coaxially connected to the platform. Therefore, in some embodiments of the present disclosure, the longitudinal space occupation of the positioning arms can be reduced, and the risk of interference and collision between the positioning arms is reduced.

In some embodiments of the present disclosure, a second cross arm (e.g., the second cross arm 122 of FIG. 1) of a positioning arm is rotatably connected to a first cross arm (e.g., the first cross arm 121 of FIG. 1 or the first cross arm 121*a* or the first cross arm 121*b* of FIG. 2) via a second rotary joint (e.g., the second rotary joint 150 of FIG. 2). Therefore, in some embodiments of the present disclosure, spatial extension of the positioning arms in a transverse direction is implemented through rotatable connection between the multiple cross arms, the risk of collision or interference between the positioning arms and a cart, another device and people, or between the positioning arms is reduced, and the space utilization is improved.

In some embodiments of the present disclosure, a positioning arm comprises a remote center motion mechanism (e.g., the remote center motion mechanisms 180 of FIGS. 8 to 10). Compared with a double parallelogram structure, the remote center motion mechanism according to some embodiments of the present disclosure can provide a more flexible design and manipulation.

The present disclosure further discloses the following embodiments:

Item 1. A remote center motion mechanism, comprising:
a first movable arm;
a first movable joint via which a proximal end of the first movable arm is rotatably connected to a mounting structure;
a second movable arm;
a second movable joint via which a distal end of the first movable arm is rotatably connected to a proximal end of the second movable arm;
a third movable joint;
a first transmission mechanism connected to the first movable joint and the second movable joint so that the first movable joint and the second movable joint rotate synchronously;
a second transmission mechanism connected to the second movable joint and the third movable joint so that the second movable joint and the third movable joint rotate synchronously; and
a third movable arm rotatably connected to a distal end of the second movable arm via the third movable joint so that a distal end of the third movable arm moves around a remote center.

Item 2. The remote center motion mechanism according to item 1, wherein the first movable joint comprises a first speed reduction wheel, the first speed reduction wheel comprises a first input shaft and a first output shaft, and the first output shaft is operable to drive the first movable joint to rotate;

the second movable joint comprises a second speed reduction wheel, the second speed reduction wheel comprises a second input shaft and a second output shaft, and the second output shaft is operable to drive the first movable joint or the second movable joint to rotate; the third movable joint comprises a third speed reduction wheel, the third speed reduction wheel comprises a third input shaft and a third output shaft, and the third output shaft is operable to drive the third movable joint to rotate; and the first transmission mechanism comprises a first transmission belt for connecting the first input shaft to the second input shaft, and the second transmission mechanism comprises a second transmission belt for connecting the second input shaft to the third input shaft.

Item 3. The remote center motion mechanism according to item 1, further comprising:

a power mechanism, wherein the power mechanism comprises:

a third electric motor comprising an output shaft; and a third transmission mechanism for connecting the output shaft of the third electric motor to the first input shaft, the second input shaft or the third input shaft.

Item 4. The remote center motion mechanism according to item 3, wherein the third transmission mechanism comprises a third transmission belt.

Item 5. The remote center motion mechanism according to item 2, further comprising:

at least one brake mechanism coupled to the first speed reduction wheel, the second speed reduction wheel or the third speed reduction wheel, and is operable to lock or unlock a corresponding speed reduction wheel.

Item 6. The remote center motion mechanism according to item 1, further comprising:

at least one angle encoder or potentiometer coupled to the first rotational joint, the second rotational joint or the third rotational joint.

Item 7, The remote center motion mechanism according to item 1, wherein the first movable arm is provided with a first strip-shaped groove, the second movable arm is provided with a second strip-shaped groove, the first strip-shaped groove and the second strip-shaped groove are respectively located in side faces of the first movable arm and the second movable arm which are away from each other, and the first transmission mechanism and the second transmission mechanism are located in the first strip-shaped groove and the second strip-shaped groove respectively.

Item 8, The remote center motion mechanism according to item 1, wherein the third movable arm comprises:

a linear movement assembly arranged on the third movable arm in a lengthwise direction of the third movable arm; and a surgical instrument mounted on the linear movement assembly and driven by the linear movement assembly to move in the lengthwise direction of the third movable arm.

Item 9. The remote center motion mechanism according to item 2, wherein the first transmission belt and the second transmission belt each comprise at least one of a transmission chain, a flexible synchronous belt or a rigid synchronous belt.

Item 10. The remote center motion mechanism according to item 2, wherein the first speed reduction wheel, the second speed reduction wheel or the third speed reduction wheel comprises a harmonic speed reducer.

Item 11. The remote center motion mechanism according to item 1, wherein reinforcing rib structures are provided in the first movable arm and/or the second movable arm.

Item 12. A surgical robot system, comprising: a remote center motion mechanism according to any one of items 1 to 11.

Item 13. The surgical robot system according to item 12, comprising:

a platform; and at least one positioning arm, each comprising a first cross arm and a first rotary joint, wherein the first rotary joint is arranged in the first cross arm or the platform, a proximal end of the first cross arm is rotatably connected to the platform via the first rotary joint, and the first cross arm is operable to rotate about a longitudinal axis relative to the platform; and a distal end of the at least one positioning arm comprises the mounting structure, and at least one remote center motion mechanism is rotatably connected to the mounting structure.

Item 14. The surgical robot system according to item 13, wherein the at least one positioning arm comprises: a first positioning arm and a second positioning arm; and a proximal end of a first cross arm of the first positioning arm and a proximal end of a first cross arm of the second positioning arm are separately connected to the platform, and the first cross arm of the first positioning arm and the first cross arm of the second positioning arm are rotatable relative to each other.

Item 15. The surgical robot system according to item 13, wherein a rotation axis of a first rotary joint of the first positioning arm is arranged coaxially with a rotation axis of a first rotary joint of the second positioning arm.

Item 16. The surgical robot system according to item 15, wherein the first rotary joint of the first positioning arm comprises:

a first electric motor fixedly arranged in the platform;

a first transmission device operable to transmit a driving force of the first electric motor; and a first speed reducer comprising a first speed reducer input shaft and a first speed reducer output shaft, wherein the first speed reducer input shaft is connected to an output shaft of the first electric motor via the first transmission device, and the first speed reducer output shaft is fixedly connected to the first cross arm of the first positioning arm and operable to drive the first cross arm of the first positioning arm to rotate.

Item 17. The surgical robot system according to item 16, wherein the first rotary joint of the second positioning arm comprises:

a second electric motor;

a second transmission device operable to transmit a driving force of the second electric motor;

a second speed reducer comprising a second speed reducer input shaft and a second speed reducer output shaft, wherein the second speed reducer input shaft is connected to an output shaft of the second electric motor via the second transmission device, and the second speed reducer output shaft is fixedly connected to the first cross arm of the second positioning arm and operable to drive the first cross arm of the second positioning arm to rotate; and a support shaft passing through the first speed reducer and having a proximal end fixedly connected to the platform and a distal end fixedly connected to the second speed reducer.

Item 18. The surgical robot system according to item 17, wherein the second speed reducer further comprises a second speed reducer transmission shaft, an end of the second speed reducer transmission shaft is arranged coaxially with and fixedly connected to the second speed reducer input shaft, and the second speed reducer transmission shaft is connected to the output shaft of the second electric motor via the second transmission device.

Item 19. The surgical robot system according to item 18, wherein the second electric motor and the second speed reducer are at least partially fixedly arranged in the first cross arm of the second positioning arm.

Item 20. The surgical robot system according to item 19, wherein the first rotary joint of the second positioning arm further comprises:

a speed reducer base fixedly arranged in the first cross arm of the first positioning arm, and fixedly connected to the distal end of the support shaft; and a proximal part of the second speed reducer is fixedly connected to the speed reducer base, a proximal end of the second speed reducer transmission shaft passes through the second speed reducer from the second speed reducer output shaft located at the distal end and is arranged coaxially with and fixedly connected to the second speed reducer input shaft located at the proximal end, and a distal end of the second speed reducer transmission shaft is connected to the output shaft of the second electric motor via the second transmission device.

Item 21. The surgical robot system according to item 17, wherein the first rotary joint of the second positioning arm comprises:

a driving module seat, comprising a base at least partially arranged in the first cross arm of the first positioning arm and a main body located at a distal end of the base and provided with a receiving cavity, wherein the distal end of the support shaft is fixedly connected to the base, and the second electric motor and the second speed reducer are fixedly arranged in the main body.

Item 22. The surgical robot system according to item 17, wherein the first rotary joint of the first positioning arm further comprises a first contracting brake, and the first contracting brake is arranged coaxially with the first speed reducer input shaft; or the first rotary joint of the second positioning arm further comprises a second contracting brake arranged coaxially on the second speed reducer output shaft.

Item 23. The surgical robot system according to item 17, wherein the first rotary joint of the first positioning arm further comprises a first angle encoder, and the first angle encoder is connected to the output shaft of the first electric motor or the first speed reducer input shaft via a transmission member; and the first rotary joint of the second positioning arm further comprises a second angle encoder, and the second angle encoder is connected to the output shaft of the second electric motor or the second speed reducer input shaft or the second speed reducer transmission shaft via a transmission member.

Item 24. The surgical robot system according to item 17, wherein the first speed reducer or the second speed reducer is a harmonic speed reducer.

Item 25. The surgical robot system according to item 17, wherein the first speed reducer and the first speed reducer input shaft comprise a through channel along a rotation axis, and the support shaft passes through the through channel to connect the first cross arm of the second positioning arm to the platform, and the first cross arm of the second positioning arm and the first cross arm of the first positioning arm are connected to the platform independently of each other.

Item 26. The surgical robot system according to item 17, wherein the platform comprises a platform frame and a support shaft base, the support shaft base is fixedly connected in the platform frame, and the proximal end of the support shaft is fixedly arranged on the support shaft base; and the first cross arm of the first positioning arm is connected to the platform frame via the first rotary joint of the first positioning arm, and the first cross arm of the second positioning arm is connected to the support shaft base via the first rotary joint of the second positioning arm.

Item 27. The surgical robot system according to item 13, wherein the at least one positioning arm further comprises at least one second cross arm and a second rotary joint, a proximal end of the at least one second cross arm is rotatably connected to a distal end of the first cross arm via the second rotary joint, and a rotation axis of the second rotary joint is parallel to a rotation axis of the first rotary joint.

It should be noted that the above are only exemplary embodiments and applied technical principles of the present disclosure. Those skilled in the art shall understand that the present disclosure is not limited to the specific embodiments herein, and various obvious changes, readjustments, and replacements can be made by those skilled in the art without departing from the scope of protection of the present disclosure. Therefore, although the present disclosure has been explained in detail through the foregoing embodiments, the present disclosure is not limited to the foregoing embodiments, and may further comprise more other equivalent embodiments without departing from the conception of the present disclosure, and the scope of the present disclosure is determined by the scope of the appended claims.

The invention claimed is:

1. A surgical robot system, comprising:

a platform; and at least one positioning arm comprising a first cross arm and a first rotary joint, wherein the first rotary joint is arranged in the first cross arm or the platform, a proximal end of the first cross arm is rotatably connected to the platform via the first rotary joint, and the first cross arm is operable to rotate about a longitudinal axis relative to the platform, wherein the at least one positioning arm comprises a first positioning arm and a second positioning arm, a proximal end of a first cross arm of the first positioning arm and a proximal end of a first cross arm of the second positioning arm are respectively connected to the platform, and the first cross arm of the first positioning arm and the first cross arm of the second positioning arm are rotatable relative to each other, wherein a rotation axis of a first rotary joint of the first positioning arm is arranged coaxially with a rotation axis of a first rotary joint of the second positioning arm, and wherein the first rotary joint of the first positioning arm comprises:

a first electric motor fixedly arranged in the platform;

a first transmission device operable to transmit a driving force of the first electric motor; and a first speed reducer comprising a first speed reducer input shaft and a first speed reducer output shaft, wherein the first speed reducer input shaft is connected to an output shaft of the first electric motor via the first transmission device, and the first speed reducer output shaft is fixedly connected to the first cross arm of the first positioning arm and operable to drive the first cross arm of the first positioning arm to rotate.

2. The surgical robot system according to claim 1, wherein the first rotary joint of the second positioning arm comprises:

a second electric motor;

a second transmission device operable to transmit a driving force of the second electric motor;

a second speed reducer comprising a second speed reducer input shaft and a second speed reducer output shaft, wherein the second speed reducer input shaft is connected to an output shaft of the second electric motor via the second transmission device, and the second speed reducer output shaft is fixedly connected to the first cross arm of the second positioning arm and operable to drive the first cross arm of the second positioning arm to rotate; and a support shaft passing through the first speed reducer and having a proximal end fixedly connected to the platform and a distal end fixedly connected to the second speed reducer.

3. The surgical robot system according to claim 2, wherein the second speed reducer further comprises a second speed reducer transmission shaft, an end of the second speed reducer transmission shaft is arranged coaxially with and fixedly connected to the second speed reducer input shaft, and the second speed reducer transmission shaft is connected to the output shaft of the second electric motor via the second transmission device.

4. The surgical robot system according to claim 3, wherein the second electric motor and the second speed reducer are at least partially fixedly arranged in the first cross arm of the second positioning arm.

5. The surgical robot system according to claim 4, wherein the first rotary joint of the second positioning arm further comprises:

a speed reducer base fixedly arranged in the first cross arm of the first positioning arm, and fixedly connected to the distal end of the support shaft; and a proximal part of the second speed reducer is fixedly connected to the speed reducer base, a proximal end of the second speed reducer transmission shaft passes through the second speed reducer from the second speed reducer output shaft located at the distal end, and is arranged coaxially with and fixedly connected to the second speed reducer input shaft located at the proximal end, and a distal end of the second speed reducer transmission shaft is connected to the output shaft of the second electric motor via the second transmission device.

6. The surgical robot system according to claim 2, wherein the first rotary joint of the second positioning arm comprises:

a driving module seat comprising a base at least partially arranged in the first cross arm of the first positioning arm and a main body located at a distal end of the base and having a receiving cavity, wherein the distal end of the support shaft is fixedly connected to the base, and the second electric motor and the second speed reducer are fixedly arranged in the main body.

7. The surgical robot system according to claim 2, wherein the first rotary joint of the first positioning arm further comprises a first contracting brake, and the first contracting brake is arranged coaxially with the first speed reducer input shaft.

8. The surgical robot system according to claim 2, wherein the first rotary joint of the first positioning arm further comprises a first angle encoder, and the first angle encoder is connected to the output shaft of the first electric motor via a transmission member; and the first rotary joint of the second positioning arm further comprises a second angle encoder, and the second angle encoder is connected to the output shaft of the second electric motor via a transmission member.

9. The surgical robot system according to claim 2, wherein the first speed reducer is a harmonic speed reducer.

10. The surgical robot system according to claim 2, wherein the first speed reducer and the first speed reducer input shaft comprise a through channel along a rotation axis, and the support shaft passes through the through channel to connect the first cross arm of the second positioning arm to the platform, and the first cross arm of the second positioning arm and the first cross arm of the first positioning arm are connected to the platform independently of each other.

11. The surgical robot system according to claim 2, wherein the platform comprises a platform frame and a support shaft base, the support shaft base is fixedly connected in the platform frame, and the proximal end of the support shaft is fixedly arranged on the support shaft base; and the first cross arm of the first positioning arm is connected to the platform frame via the first rotary joint of the first positioning arm, and the first cross arm of the second positioning arm is connected to the support shaft base via the first rotary joint of the second positioning arm.

12. The surgical robot system according to claim 2, wherein the first rotary joint of the second positioning arm further comprises a second contracting brake arranged coaxially on the second speed reducer output shaft.

13. The surgical robot system according to claim 2, wherein:

the first rotary joint of the first positioning arm further comprises a first angle encoder, and the first angle encoder is connected to the first speed reducer input shaft via a transmission member; and the first rotary joint of the second positioning arm further comprises a second angle encoder, and the second angle encoder is connected to the second speed reducer input shaft or the second speed reducer transmission shaft via a transmission member.

14. The surgical robot system according to claim 2, wherein the second speed reducer is a harmonic speed reducer.

15. The surgical robot system according to claim 1, wherein the at least one positioning arm further comprises at least one second cross arm and a second rotary joint, a proximal end of the at least one second cross arm is rotatably connected to a distal end of the first cross arm via the second rotary joint, and a rotation axis of the second rotary joint is parallel to a rotation axis of the first rotary joint.

16. The surgical robot system according to claim 15, wherein the at least one positioning arm further comprises a vertical arm and a vertical arm rotary joint, the vertical arm comprises a vertical arm outer cylinder and a vertical arm inner cylinder which are movable relative to each other in a longitudinal direction, and one of the vertical arm outer cylinder and the vertical arm inner cylinder is connected to a distal end of the second cross arm via the vertical arm rotary joint, to rotate about the longitudinal axis relative to the distal end of the second cross arm.

17. The surgical robot system according to claim 16, wherein the at least one positioning arm further comprises an inclined arm and an inclined arm rotary joint, wherein a proximal end of the inclined arm is connected to a distal end of the vertical arm via the inclined arm rotary joint, and a rotation axis of the inclined arm rotary joint is angled relative to the longitudinal direction.

18. The surgical robot system according to claim 17, wherein the at least one positioning arm further comprises a remote center motion mechanism, the remote center motion mechanism comprising:

a first movable arm;

a first movable joint via which a proximal end of the first movable arm is rotatably connected to a distal end of the inclined arm;

a second movable arm;

a second movable joint via which a distal end of the first movable arm is rotatably connected to a proximal end of the second movable arm;

a third movable joint;

a first transmission mechanism connected to the first movable joint and the second movable joint so that the first movable joint and the second movable joint rotate synchronously;

a second transmission mechanism connected to the second movable joint and the third movable joint so that the second movable joint and the third movable joint rotate synchronously; and a third movable arm rotatably connected to a distal end of the second movable arm via the third movable joint so that a distal end of the third movable arm moves around a remote center point.

19. The surgical robot system according to claim 18, wherein the first movable joint comprises a first speed reduction wheel, the first speed reduction wheel comprises a first input shaft and a first output shaft, and the first output shaft is operable to drive the first movable joint to rotate;

the second movable joint comprises a second speed reduction wheel, the second speed reduction wheel comprises a second input shaft and a second output shaft, and the second output shaft is operable to drive the first movable joint or the second movable joint to rotate;

the third movable joint comprises a third speed reduction wheel, the third speed reduction wheel comprises a third input shaft and a third output shaft, and the third output shaft is operable to drive the third movable joint to rotate; and the first transmission mechanism comprises a first transmission belt for connecting the first input shaft to the second input shaft, and the second transmission mechanism comprises a second transmission belt for connecting the second input shaft to the third input shaft.

20. The surgical robot system according to claim 1, comprising at least two groups of positioning arms, wherein each group of positioning arms comprises the first positioning arm and the second positioning arm, and the at least two groups of positioning arms are in mirror symmetry with respect to a symmetry plane of the platform.

\* \* \* \* \*